(12) United States Patent
Ogino et al.

(10) Patent No.: US 6,242,452 B1
(45) Date of Patent: Jun. 5, 2001

(54) 7-AMINOPYRIDO[2,3-D]PYRIMIDINE DERIVATIVES

(75) Inventors: Takashi Ogino; Kazuhito Furukawa, both of Katoh-gun (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/418,982

(22) Filed: Oct. 14, 1999

(30) Foreign Application Priority Data

Oct. 15, 1998 (JP) .................................................. 10-293250

(51) Int. Cl.$^7$ .......................... A61K 31/505; A61P 11/06; C07D 239/96; C07D 471/04

(52) U.S. Cl. ............................................. 514/258; 544/279

(58) Field of Search ............................... 544/279; 514/258

(56) References Cited

U.S. PATENT DOCUMENTS

| | | | |
|---|---|---|---|
| 3,235,554 | * 2/1966 | Papesch et al. ....................... | 544/279 |
| 3,272,816 | * 9/1966 | Papesch et al. ....................... | 544/279 |
| 3,275,634 | 9/1966 | Papesch ................................ | 544/279 |
| 4,808,587 | 2/1989 | Go et al. .............................. | 544/279 |
| 5,264,437 | 11/1993 | Wilhelm et al. ....................... | 544/279 |
| 5,776,942 | * 7/1998 | Furukawa et al. .................... | 544/279 |

FOREIGN PATENT DOCUMENTS

| | | |
|---|---|---|
| 2317230 | 10/1973 | (DE) . |
| 2334266 | 1/1974 | (DE) . |
| 0 163 599 A2 | 12/1985 | (EP) . |
| 0 260 817 A1 | 3/1988 | (EP) . |
| 0 243 311 B1 | 6/1993 | (EP) . |
| 0 696 590 A1 | 2/1996 | (EP) . |
| 989048 | 4/1965 | (GB) . |
| 63-45279 | 2/1988 | (JP) . |
| 7/504676 | 5/1995 | (JP) . |
| 92/08719 | 5/1992 | (WO) . |
| WO 93/19068 | 9/1993 | (WO) . |

OTHER PUBLICATIONS

Muller T., et al., "Subtypes of the type 4 cAMP phosphodiesterases: structure, regulation and selective inhibition", *Trends in Pharmacological Sciences, GB, Elsevier Trends Journal*, Cambridge, vol. 17, No. 8, Aug. 1, 1996, pp. 294–298, XP004034578.

Kaneko et al., "Elevated Intracellular Cyclic Amp Inhibits Chemotaxis in Human Eosinophils, " *Cellular Signalling*, vol. 7, No. 5, pp. 527–534, 1995.

Alvarez et al., "Activation and Selective Inhibition of a Cyclic AMP–Specific Phosphodiesterase, PDE–4D3" *Molecular Pharmacology*, 48:616–622 (1995).

Lowe, III, et al., "Structure–Activity Relationship of Quinazolinedione Inhibitors of Calcium–Independent Phosphodiesterase" *J. Med. Chem.* 1991, 34, 624–628.

Verghese et al., "Differential Regulation of Human Monocyte–Derived TNFα and IL–1β by Type IV cAMP–Phosphodiesterase (cAMP–PDE) Inhibitors" *The Journal of Pharmacology and Experimental Therapeutics*, vol. 272, No. 3, pp. 1313–1320, 1995.

(List continued on next page.)

*Primary Examiner*—Richard L. Raymond
*Assistant Examiner*—Venkutaraman Balasubramanian
(74) *Attorney, Agent, or Firm*—Hollander Law Firm, P.L.C.

(57) ABSTRACT

Compounds which exhibit excellent bronchodilating action with low side effects and are 7-amino-1-phenylpyrido[2,3-d]pyrimidine-2,4-dione derivatives represented by the formula (I) or a pharmaceutically acceptable salt or hydrate thereof:

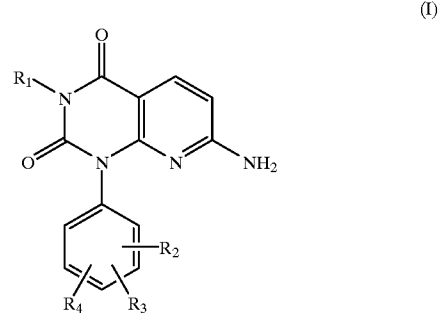

(I)

wherein $R_1$ is hydrogen, lower alkenyl, phenyl or lower alkyl which is optionally substituted with a substituent selected from the following substituents(a) to (i);

(a) oxo,
(b) lower alkoxy,
(c) phenyl which is optionally substituted with one or more lower alkyl, lower alkoxy, carboxyl, lower alkoxycarbonyl, mercapto, halogen, trifluoromethyl and/or nitro;
(d) naphthyl,
(e) furyl,
(f) isoxazolyl which is optionally substituted with one or more lower alkyl,
(g) pyridyl which is optionally substituted with one or more lower alkyl and/or halogen,
(h) thienyl which is optionally substituted with halogen, and
(i) 1,3-dioxolanyl;

and $R_2$, $R_3$ and $R_4$ each independently is hydrogen, halogen, lower alkoxy, benzyloxy, carboxyl or lower alkoxycarbonyl. The compounds of the present invention exhibit unexpectedly superior bronchodilating action, safety, and rapid transfer into the blood stream and prolonged half life in the blood stream. Accordingly, the compounds and pharmaceutical compositions containing them are useful as therapeutic agents for bronchial asthma.

27 Claims, No Drawings

OTHER PUBLICATIONS

Chemical Abstracts, vol. 102, No. 15, Apr. 15, 1985, pp. 625–626, abstract No. 131985x; T .L. Su, et al., "Pyrimidines, 21. Novel reactions of 5–cyano–1,3–dimethyluracil with carbon nucleophiles. A facile preparation of certain pyrido(2,3–d)pyrimidines".

Chemical Abstracts, vol. 93, No. 9, Sep. 1, 1980, pp. 643–644, abstract No. 95234m; S. Brunel, et al.: "Synthesis of new 1H,3H–pyrido(2,3–d)pyrimidine–2,4–diones".

Chemical Abstracts, vol. 100, No. 9, Feb. 27, 1984, p. 596, abstract No. 68254z, T. Itoh, et al.: "A simple synthesis of 1,3–dialkylpyrido(2,3–d)pyrimidines".

Tominaga, et al., Chemical Abstracts, vol. 100, No. 209737y (1984).

Matyus, et al., Chemical Abstracts, vol. 102, No. 6405g (1985).

Rodgers, et al., Chemical Abstracts, vol. 106, No. 156415g (1987).

Chemical and Pharmaceutical Bulletin, vol. 33, No. 4, 1985, pp. 1375–1379; T. Itoh, et al.:"A simple synthesis of 1,3–dialkylpyrido(2,3–d)pyrimidines".

McLean, et al., *J. Chem. Soc.*, pp. 2582–2585 (1949).

Cherdantseva, N.M., et al., "Synthesis of pyrido[2,3–]pyrimidines on the basis of 5–formyl–6–aminouracils", Chem. Heterocycl. Compounds, vol. 19, No. 6, 1983, pp. 674–677.

Rodgers, G.R., et al., "Linear expanded xanthines", Monatshefte fur Chemie (Chemical Monthly), vol. 117, 1986, pp. 879–882.

Burova, O.A., et al., "Pyrido[2,3–d]pyrimidines. 7. Reactions of 1,3–dimethyl–5, 7–dichloro–6–nitropyrido[2,3–d] pyrimidine–2,4–dione with amines. Synthesis of derivatives of triazolo(4',5':4,5)pyrido[2,3–d]pyrimidine", Chem. Heterocycl. Compounds, vol. 29, No. 3, 1993, pp. 335–338.

Heber, D., et al., "Synthesis and positive inotropic activity of several 5–aminopyrido[2,3–d]pyridmidines", Die Pharmazie, vol. 48, No. 7, Jul. 1993, pp. 509–513.

Heber, D., et al., "Positive inotropic activity of 5–amino–6–cyano–1,3–dimethyl–1,2,3,4–tetrahydropyrido [2,3–d]pyrimidine–2,4–dione in cardiac muscle from guinea–pig and man", Die Pharmazie, vol. 48, No. 7, Jul. 1993, pp. 537–541.

Goto, et al., "Anti–anaphylactic activities of a new benzopyranopyridine derivatives Y–12, 141 in rats and guinea pigs", Japan. J. Pharmacol. 30, 1980, pp. 537–547.

Su, et al., "Pyrimidines, 21, Novel reactions of 5–cyano–1, 3–dimethyluracil with carbon nucleophiles. A facile preparation of certain pyrido[2,3–d]pyrimidines (1)", J. Heterocycl. Chem. 1984, 21, pp. 1543–1547.

\* cited by examiner

7-AMINOPYRIDO[2,3-D]PYRIMIDINE DERIVATIVES

FIELD OF THE INVENTION

The present invention relates to novel 7-amino-1-phenylpyrido[2,3-d]pyrimidine-2,4-dione derivatives and medical uses thereof.

BACKGROUND OF THE INVENTION

An allergy is a pathological condition where a living body is damaged by an immune response although the response is originally a biological defense reflex. Allergic rhinitis is divided broadly into two groups. Namely, one group is perennial rhinitis caused by house dust or by mites and another group is pollinosis linked with high amounts of airborne pollen whereby many people are affected. There is a difference in symptoms between the two groups of allergies and, therefore, therapeutic methods are different. Unfortunately, once a person suffers from allergic disease, natural healing at an early stage cannot be expected and no therapeutic method to cure it completely has been established yet. Therefore, the number of patients in need of treatment is cumulatively increasing.

Bronchial asthma is a disease which is characterized by a paroxysmal dyspnea accompanied by coughs and wheezes. Although its cause is ambiguous, a theory that it is a chronic inflammatory disease of the airway has been established recently in addition to the already proposed theory of reversible obstructive impairment and hypersensitivity of the airway. Accordingly, in current therapy, steroidal preparations are used with an object of suppression of inflammation of the airway. Also, since the disease is also accompanied by an airway obstruction, anti-chemical mediators or bronchial dilators are used jointly.

Steroidal preparations used by means of inhalation, oral administration, intravenous injection, etc. are pharmaceuticals which exhibit various side effects together with a sharp clinical effect. Their main known side effects include, induction of infectious diseases, osteoporosis, arteriosclerosis, diabetes mellitus, mental disorder and moon face. It is said that serious side effects occur when administration of a steroidal preparation extends over a long period and that frequency and degree of seriousness of adrenal insufficiency is dependent upon the dose and term of the administration. Especially, withdrawal symptoms occur upon a rapid reduction of the administered dose. Additional problems include adrenal insufficiency by adrenal cortical shrinkage due to administration of high doses for a long period.

Anti-chemical mediators are pharmaceuticals which inhibit the biosynthesis and liberation of chemical mediators participating in allergy such as histamine, thromboxane and leukotriene, or pharmaceuticals which antagonize the binding of such chemical mediators to receptors. Thus, such anti-chemical mediators are not direct therapeutic agents for dilating the shrunken or contracted airway of asthma and for improving the dyspnea. They are used as pharmaceuticals for preventing the onset of asthma symptoms caused by chemical mediators.

Bronchialdilators are $\beta_2$ stimulants and theophylline preparations are used as rapid-acting therapeutic agents for relieving the dyspnea symptom of asthma. In the case of the onset of severe asthma, therapies such as a subcutaneous injection of a $\beta_2$ stimulant and a continuous intravenous drip of theophylline are carried out. However, in the treatment with a $\beta_2$ stimulant, there is a problem of death by suffocation from a negative feedback due to its abuse. The theophylline preparation also has a disadvantage in that its safety region is narrow and, at high concentrations, occurrence of toxic symptoms, headache, vomiting, pulsation and extrasystole takes place. Accordingly, at present, caution for abuse is required for $\beta_2$ stimulants, and a therapeutic drug monitoring (TDM) is carried out for theophylline preparations.

As mentioned above, the already-known therapeutic agents for bronchial asthma have both merits and demerits in terms of onset of the effect and generation of side effects. Therefore, in the practical clinical field, there has been a demand for safer, more rapidly acting pharmaceuticals.

Compounds having a pyrido[2,3-d]pyrimidine structure which have an anti-allergic action are disclosed in Japanese Laid-Open Patent Publication Sho-63/45279 and corresponding U.S. Pat. No. 4,808,587 to Go et al. Compounds having a 7-aminopyrido[2,3-d]pyrimidine structure which show a bronchial dilating action are disclosed in Japanese Laid-Open Patent Publications Hei-8/3046, Hei-8/3164 and Hei-8/3165 and their corresponding U.S. Pat. No. 5,776,942. However, in those known compounds, separation of pharmaceutical effect from side effects is not sufficient. Also, the bronchial dilating action of the known compounds is not satisfactory whereby they have not been allowed as pharmaceuticals for actual use. Additional compounds having a pyrido[2,3-d]pyrimidine structure have been reported in Japanese Laid-Open Patent Publication Hei-7/504676; *Cell Signaling*, 7, 527 (1995); *Mol. Pharmacol.*, 48, 616 (1995); *J. Med. Chem.*, 34, 624 (1991); and *J. Pharmacol. Exp. Ther.*, 272, 3,1313 (1995)). However, these compounds are problematic in terms of their behavior in vivo such as exhibiting poor transfer into blood. None of them have been commercialized as pharmaceuticals.

None of the references disclose 7-amino-1-phenylpyrido[2,3-d]pyrimidine-2,4-dione derivatives according to the present invention. The present invention solves the above-mentioned problems and provides a therapeutic agent for bronchial asthma which is highly desirable by patients and by the medical field, i.e. an agent having high safety, rapid action, and good behavior in vivo.

SUMMARY OF THE INVENTION

The present inventors have carried out an intensive investigation of 7-aminopyrido[2,3-d]pyrimidine derivatives and have found that 7-amino-1-phenylpyrido[2,3-d]-pyrimidine-2,4-dione derivatives have an excellent bronchial dilating action, have high safety and little side effect and exhibit good behavior in vivo whereupon the present invention has been achieved. Consequently, the compounds of the present invention are very useful as therapeutic agents for bronchial asthma.

The 7-amino-1-phenylpyrido[2,3-d]-pyrimidine-2,4-dione derivatives of the present invention which are contained as an effective component in the pharmaceutical compositions of the present invention for the treatment of bronchial asthma are represented by formula (I):

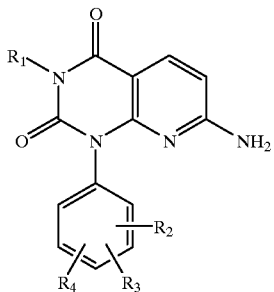

(I)

wherein $R_1$ is hydrogen, lower alkenyl, phenyl or lower alkyl which is optionally substituted with a substituent selected from the following substituents (a) to (i):

(a) oxo, (b) lower alkoxy, (c) phenyl which is optionally substituted with at least one member selected from the group consisting of lower alkyl, lower alkoxy, carboxyl, lower alkoxycarbonyl, mercapto, halogen, trifluoromethyl and nitro;

(d) naphthyl, (e) furyl, (f) isoxazolyl which is optionally substituted with one or more lower alkyl, (g) pyridyl which is optionally substituted with one or more lower alkyl and/or halogen, (h) thienyl which is optionally substituted with halogen, and (i) 1,3-dioxolanyl;

and $R_2$, $R_3$ and $R_4$ each independently is hydrogen, halogen, lower alkoxy, benzyloxy, carboxyl or lower alkoxycarbonyl.

The derivatives of the present invention also include pharmaceutically acceptable salts and metal complexes of the compounds represented by general formula (I). The present invention also provides pharmaceutical compositions containing pharmaceutically effective amounts of at least one of said derivatives as an effective component.

DETAILED DESCRIPTION OF THE INVENTION

The present invention provides 7-amino-1-phenylpyrido[2,3-d]pyrimidine-2,4-dione derivatives which exhibit unexpectedly superior bronchodilating action, safety, and rapid transfer into the blood stream and prolonged half life in the blood stream. Accordingly, the compounds and pharmaceutical compositions containing them as an effective component are useful as therapeutic agents for bronchial asthma. The compounds of the present invention include 7-amino-1-phenylpyrido[2,3-d]pyrimidine-2,4-dione derivatives represented by the following formula (I) and pharmaceutically acceptable salts and hydrates thereof:

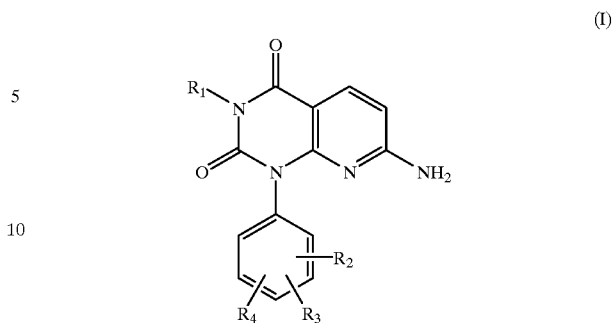

(I)

wherein $R_1$ is hydrogen, lower alkenyl, phenyl or lower alkyl which is optionally substituted with a substituent selected from the following substituents (a) to (i);

(a) oxo, (b) lower alkoxy, (c) phenyl which is optionally substituted with one or more lower alkyl, lower alkoxy, carboxyl, lower alkoxycarbonyl, mercapto, halogen, trifluoromethyl and/or nitro;

(d) naphthyl, (e) furyl, (f) isoxazolyl which is optionally substituted with one or more lower alkyl, (g) pyridyl which is optionally substituted with one or more lower alkyl and/or halogen, (h) thienyl which is optionally substituted with halogen, and (i) 1,3-dioxolanyl;

and $R_2$, $R_3$ and $R_4$ each independently is hydrogen, halogen, lower alkoxy, benzyloxy, carboxyl or lower alkoxycarbonyl.

In the formula, "lower alkyl" means a linear or branched alkyl preferably having 1 to 6 carbon atoms such as methyl, ethyl, propyl, isopropyl, butyl, isobutyl, sec-butyl or t-butyl, pentyl, isopentyl, neopentyl, t-pentyl, hexyl, isohexyl, dimethylbutyl. Also, "lower alkoxy" represents a linear or branched alkoxy preferably having 1 to 6 carbon atoms such as methoxy, ethoxy, propoxy, isopropoxy, butoxy, isobutoxy, sec-butoxy or t-butoxy, pentyloxy, isopentyloxy, neopentyloxy, t-pentyloxy, hexyloxy, isohexyloxy, dimethylbutoxy. "Halogen" is preferably fluoro, chloro, bromo, or iodo. "Lower alkenyl" means a linear or branched alkenyl preferably having 2 to 6 carbon atoms such as ethenyl, propenyl, butenyl, pentenyl, or hexenyl.

Preferred embodiments of the present invention are:

(1) A 7-amino-1-phenylpyrido[2,3-d]pyrimidine-2,4-dione derivative represented by the above formula (I) and pharmaceutically acceptable salts and hydrates thereof.

(2) A 7-amino-1-phenylpyrido[2,3-d]pyrimidine-2,4-dione derivative according to paragraph (1) wherein $R_2$ is hydrogen.

(3) A 7-amino-1-phenylpyrido[2,3-d]pyrimidine-2,4-dione derivative according to paragraph (2) wherein $R_3$ is lower alkoxy.

(4) A 7-amino-1-phenylpyrido[2,3-d]pyrimidine-2,4-dione derivative according to paragraph (3) wherein $R_3$ is substituted at a meta position.

(5) A 7-amino-1-phenylpyrido[2,3-d]pyrimidine-2,4-dione derivative according to any one of paragraphs (3) to (4) wherein the lower alkoxy is methoxy.

(6) A 7-amino-1-phenylpyrido[2,3-d]pyrimidine-2,4-dione derivative according to any one of paragraphs (3) to (5) wherein $R_4$ is lower alkoxy.

(7) A 7-amino-1-phenylpyrido[2,3-d]pyrimidine-2,4-dione derivative according to paragraph (6) wherein $R_4$ is substituted at a meta position.

(8) A 7-amino-1-phenylpyrido[2,3-d]pyrimidine-2,4-dione derivative according to any one of paragraphs (6) to (7) wherein the lower alkoxy is methoxy.

(9) A 7-amino-1-phenylpyrido[2,3-d]pyrimidine-2,4-dione derivative according to any one of paragraphs (1) to (8) wherein $R_1$ is lower alkyl.

(10) A 7-amino-1-phenylpyrido[2,3-d]pyrimidine-2,4-dione derivative according to paragraph (9) wherein the lower alkyl is isobutyl.

(11) A therapeutic agent for bronchial asthma containing a 7-amino-1-phenylpyrido[2,3-d]pyrimidine-2,4-dione derivative according to any one of paragraphs (1) to (10) as an effective component.

(12) A bronchialdilatorcontaining a 7-amino-1-phenylpyrido[2,3-d]pyrimidine-2,4-dione derivative according to any one of paragraphs (1) to (10) as an effective component.

Especially preferred compounds of the present invention are:

7-amino-1,2,3,4-tetrahydro-1,3-diphenylpyrido[2,3-d]pyrimidine-2,4-dione (Compound 1)

7-amino-3-ethyl-1,2,3,4-tetrahydro-1-phenylpyrido[2,3-d]pyrimidine-2,4-dione (Compound 2)

7-amino-1,2,3,4-tetrahydro-1-phenyl-3-propylpyrido[2,3-d]pyrimidine-2,4-dione (Compound 3)

7-amino-3-butyl-1,2,3,4-tetrahydro-1-phenylpyrido[2,3-d]pyrimidine-2,4-dione (Compound 4)

7-amino-3-ethyl-1-(3,5-dimethoxyphenyl)-1,2,3,4-tetrahydropyrido[2,3-d]pyrimidine-2,4-dione (Compound 5)

7-amino-1-(3,5-dimethoxyphenyl)-1,2,3,4-tetrahydro-3-propylpyrido[2,3-d]pyrimidine-2,4-dione (Compound 6)

7-amino-3-butyl-1-(3,5-dimethoxyphenyl)-1,2,3,4-tetrahydropyrido[2,3-d]pyrimidine-2,4-dione (Compound 7)

7-amino-3-benzyl-1-(3,5-dimethoxyphenyl)-1,2,3,4-tetrahydropyrido[2,3-d]pyrimidine-2,4-dione (Compound 8)

7-amino-1,2,3,4-tetrahydro-1-(4-methoxyphenyl)-3-propylpyrido[2,3-d]pyrimidine-2,4-dione (Compound 9)

7-amino-3-butyl-1,2,3,4-tetrahydro-1-(4-methoxyphenyl)pyrido[2,3-d]pyrimidine-2,4-dione (Compound 10)

7-amino-3-benzyl-1,2,3,4-tetrahydro-1-(4-methoxyphenyl)pyrido[2,3-d]pyrimidine-2,4-dione (Compound 11)

7-amino-1,2,3,4-tetrahydro-1-(4-methoxyphenyl)-3-(4-picolyl)pyrido[2,3-d]pyrimidine-2,4-dione (Compound 12)

7-amino-1-(3,4-dimethoxyphenyl)-1,2,3,4-tetrahydro-3-propylpyrido[2,3-d]pyrimidine-2,4-dione (Compound 13)

7-amino-1-(2,5-dimethoxyphenyl)-1,2,3,4-tetrahydro-3-propylpyrido[2,3-d]pyrimidine-2,4-dione (Compound 14)

7-amino-1-(3,5-dimethoxyphenyl)-1,2,3,4-tetrahydro-3-propylpyrido[2,3-d]pyrimidine-2,4-dione (Compound 15)

7-amino-3-benzyl-1,2,3,4-tetrahydro-1-phenylpyrido[2,3-d]pyrimidine-2,4-dione (Compound 16)

7-amino-1,2,3,4-tetrahydro-1-phenyl-3-(4-picolyl) pyrido [2,3-d]pyrimidine-2,4-dione (Compound 17)

7-amino-1-(3,5-dimethoxyphenyl)-1,2,3,4-tetrahydro-3-(4-picolyl)pyrido[2,3-d]pyrimidine-2,4-dione (Compound 18)

7-amino-3-benzyl-1-(2,4-dimethoxyphenyl)-1,2,3,4-tetrahydropyrido[2,3-d]pyrimidine-2,4-dione (Compound 19)

7-amino-1-(3,5-dimethoxyphenyl)-3-(2-ethoxyethyl)-1,2,3,4-tetrahydropyrido[2,3-d]pyrimidine-2,4-dione (Compound 20)

7-amino-3-(3-butenyl)-1-(3,5-dimethoxyphenyl)-1,2,3,4-tetrahydropyrido[2,3-d]pyrimidine-2,4-dione (Compound 21)

Methyl [7-amino-1,2,3,4-tetrahydro-3-(4-picolyl)-2,4-dioxopyrido[2,3-d]pyrimidine-1-yl]-3-benzoate (Compound 22)

7-amino-3-(4-chlorobenzyl)-1,2,3,4-tetrahydro-1-phenylpyrido [2,3-d]pyrimidine-2,4-dione (Compound 23)

7-amino-1,2,3,4-tetrahydro-3-(3-(2-methyl) picolyi)-1-phenylpyrido[2,3-d]pyrimidine-2,4-dione (Compound 24)

7-amino-1,2,3,4-tetrahydro-3-(2-picolyl)-1-phenylpyrido[2,3-d]pyrimidine-2,4-dione (Compound 25)

7-amino-1,2,3,4-tetrahydro-3-(3-picolyl) -1-phenylpyrido[2,3-d]pyrimidine-2,4-dione (Compound 26)

7-amino-3-(3-chlorobenzyl)-1,2,3,4-tetrahydro-1-phenylpyrido[2,3-d]pyrimidine-2,4-dione (Compound 27)

7-amino-1,2,3,4-tetrahydro-3-(4-methoxybenzyl)-1-phenylpyrido[2,3-d]pyrimidine-2,4-dione (Compound 28)

7-amino-3-(4-fluorobenzyl)-1,2,3,4-tetrahydro-1-phenylpyrido[2,3-d]pyrimidine-2,4-dione (Compound 29)

7-amino-1,2,3,4-tetrahydro-3-(4-methybenzyl)-1-phenylpyrido[2,3-d]pyrimidine-2,4-dione (Compound 30)

7-amino-1,2,3,4-tetrahydro-3-(3-nitrobenzyl)-1-phenylpyrido[2,3-d]pyrimidine-2,4-dione (Compound 31)

7-amino-3-(2-chlorobenzyl)-1,2,3,4-tetrahydro-1-phenylpyrido [2,3-d]pyrimidine-2,4-dione (Compound 32)

7-amino-1,2,3,4-tetrahydro-3-(3-methybenzyl)-1-phenylpyrido [2,3-d]pyrimidine-2,4-dione (Compound 33)

7-amino-3-(3,4-dichlorobenzyl)-1,2,3,4-tetrahydro-1-phenylpyrido [2,3-d]pyrimidine-2,4-dione (Compound 34)

7-amino-1,2,3,4-tetrahydro-3-(3-methoxybenzyl)-1-phenylpyrido[2,3-d]pyrimidine-2,4-dione (Compound 35)

7-amino-1,2,3,4-tetrahydro-3-(4-trifluoromethylbenzyl)-1-phenylpyrido[2,3-d]pyrimidine-2,4-dione (Compound 36)

7-amino-1,2,3,4-tetrahydro-1-phenyl-3-(2-thienylmethyl) pyrido [2,3-d]pyrimidine-2,4-dione (Compound 37)

7-amino-3-(2-furfuryl)-1,2,3,4-tetrahydro-1-phenylpyrido [2,3-d]pyrimidine-2,4-dione (Compound 38)

7-amino-1,2,3,4-tetrahydro-1-phenyl-3-(3-thienylmethyl) pyrido [2,3-d]pyrimidine-2,4-dione (Compound 39)

7-amino-3-(3-(2-chloro-6-methyl)picolyl)-1,2,3,4-tetrahydro-1-phenylpyrido[2,3-d]pyrimidine-2,4-dione (Compound 40)

Methyl 4-[7-amino-1,2,3,4-tetrahydro-1-phenyl-2,4-dioxopyrido [2,3-d]pyrimidine-3-yl-methyl]benzoate (Compound 41)

7-amino-3-(2-dioxolanylmethyl)-1,2,3,4-tetrahydro-1-phenylpyrido[2,3-d]pyrimidine-2,4-dione (Compound 42)

4-[7-amino-1,2,3,4-tetrahydro-1-phenyl-2,4-dioxopyrido[2,3-d]pyrimidine-3-yl-methyl]benzoic acid (Compound 43)

7-amino-3-benzyl-1-(3-chlorophenyl)-1,2,3,4-tetrahydropyrido[2,3-d]pyrimidine-2,4-dione (Compound 44)

7-amino-1,2,3,4-tetrahydro-3-(4-nitrobenzyl)-1-phenylpyrido[2,3-d]pyrimidine-2,4-dione (Compound 45)

7-amino-1,2,3,4-tetrahydro-3-(2-methoxybenzyl)-1-phenylpyrido [2,3-d]pyrimidine-2,4-dione (Compound 46)

7-amino-3-(3,5-dimethoxybenzyl)-1,2,3,4-tetrahydro-1-phenylpyrido[2,3-d]pyrimidine-2,4-dione (Compound 47)

7-amino-3-(5-chlorothienylmethyl)-1,2,3,4-tetrahydro-1-phenylpyrido[2,3-d]pyrimidine-2,4-dione (Compound 48)

7-amino-3-benzyl-1-(3,5-difluorophenyl)-1,2,3,4-tetrahydropyrido[2,3-d]pyrimidine-2,4-dione (Compound 49)

7-amino-1,2,3,4-tetrahydro-3-(1-naphthylmethyl)-1-phenylpyrido[2,3-d]pyrimidine-2,4-dione (Compound 50)

7-amino-1,2,3,4-tetrahydro-3-(3,5-dimethylbenzyl)-1-phenylpyrido[2,3-d]pyrimidine-2,4-dione (Compound 51)

7-amino-3-benzyl-1,2,3,4-tetrahydro-1-(3-methoxyphenyl) pyrido[2,3-d]pyrimidine-2,4-dione (Compound 52)

7-amino-3-(4-bromobenzyl)-1,2,3,4-tetrahydro-1-phenylpyrido[2,3-d]pyrimidine-2,4-dione (Compound 53)

7-amino-3-(3-(2-chloro)picolyl)-1,2,3,4-tetrahydro-1-phenylpyrido[2,3-d]pyrimidine-2,4-dione (Compound 54)

7-amino-3-benzyl-1-(3-benzyloxyphenyl)-1,2,3,4-tetrahydropyrido[2,3-d]pyrimidine-2,4-dione (Compound 55)

7-amino-1,2,3,4-tetrahydro-3-(3-methylisoxazol-5-yl-methyl)-1-phenylpyrido[2,3-d]pyrimidine-2,4-dione (Compound 56)

7-amino-3-(3,5-dimethylisoxazol-4-yl-methyl)-1,2,3,4-tetrahydro-1-phenylpyrido[2,3-d]pyrimidine-2,4-dione (Compound 57)

7-amino-1,2,3,4-tetrahydro-1-phenyl-3-(5-phenylpentyl) pyrido[2,3-d]pyrimidine-2,4-dione (Compound 58)

Of the above compounds of the present invention, the most preferred compound is 7-amino-1-(3,5-dimethoxyphenyl)-1,2,3,4-tetrahydro-3-propylpyrido[2,3-d]pyrimidine-2,4-dione (Compound 15).

The 7-amino-1-phenylpyrido[2,3-d]pyrimidine-2,4-dione derivatives of the present invention include the pharmaceutically acceptable salts of the compounds represented by the above-given formula (I) such as acid addition salts with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; salts with alkali metals such as sodium or potassium, salts with alkaline-earth metals such as calcium or magnesium, or salts with other metals such as aluminum; or salts with bases such as ammonia or organic amines. The salts may be manufactured by known methods from the compounds of the present invention in a free state or may be mutually converted among the salts by conventional means.

The present invention includes any and all stereoisomers or steric isomers such as cis-trans isomers, optical isomers, and conformational isomers and hydrates of the compounds of the present invention.

The compounds of the present invention, which include the 7-amino-1-phenylpyrido[2,3-d]pyrimidine-2,4-dione derivatives represented by the formula (I) and pharmaceutically acceptable salts and hydrates thereof, can be made into pharmaceutical preparations by combining one or more of the compounds with at least one pharmaceutically acceptable carrier or diluent. Any of the known methods for providing preparations, such as for oral or parenteral administrations (e.g. solids, semi-solids, liquids, or gases) may be used to produce the pharmaceutical compositions of the present invention. For example, for oral administrations tablets, capsules, powders, liquids, etc. may be employed. Parenteral administrations may be subcutaneous, intravenous, intramuscular, intrarectal and intranasal administrations. In preparing the preparations, the 7-amino-1-phenylpyrido[2,3-d]pyrimidine-2,4-dione derivatives of the present invention may be used in the form of their pharmaceutically acceptable salts. The compounds of the present invention may be used either solely or jointly in pharmaceutically effective amounts for treating animals or humans. The compounds of the invention can be used either solely or jointly together in pharmaceutically acceptable amounts with pharmaceutically effective amounts of other pharmaceutically active components in pharmaceutical compositions or preparations.

In the case of preparations for oral administration, one or more of the compounds of the present invention either alone or in combination with commonly-used pharmaceutically acceptable excipients in pharmaceutically acceptable amounts such as at least one suitable pharmaceutically acceptable additive or carrier (e.g. lactose, mannitol, corn starch, potato starch, potassium citrate, etc.) may be mixed with one or more pharmaceutically acceptable: (1) binders such as cellulose derivatives (e.g. crystalline cellulose, cellulose, hydroxypropylcellulose, etc.), gum arabicum, corn starch, gelatin, etc., (2) disintegrating agents such as corn starch, potato starch, potassium carboxymethylcellulose, calcium carboxymethylcellulose, etc., (3) lubricating agents such as talc, magnesium stearate, etc. and (4) other pharmaceutically acceptable excipients including pharmaceutically acceptable bulking agents, moisturizing agents, buffers, preservatives, perfumes and the like to obtain tablets, diluted powders, granules or capsules.

Alternatively, suppositories may be prepared by mixing at least one compound of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of injections, it is possible to prepare solutions or suspensions of one or more compounds of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc.

In the case of inhalations or aerosol preparations, at least one compound of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

It is also possible, depending upon the type of the disease, to prepare pharmaceutical preparations other than the above-mentioned ones which are suitable for therapy depending upon the state of the patient. Exemplary of other pharmaceutical preparations are syrups, collyriums, medicines for external use (e.g. ointments, gels, poultices), etc.

The preferred dosage of the compound of the present invention varies depending upon the subject to be administered (age, body weight, symptoms, etc. of the patient), form of the preparation, method for the administration, term for the administration, etc. To achieve the desired result, the compound may be usually administered by the oral route with a daily dose of 0.001–50 mg per day, preferably 0.05–25 mg per day, to common adults.

In the case of a parenteral administration such as by injection, the preferred dosage, may be from ⅓ to ⅟₁₀ of the above-mentioned oral dosages because of the effects of absorption, etc. in the oral route.

The compounds of the present invention may be manufactured according to methods described in: a) Japanese Laid-Open Patent Publication Sho-63/45279 and corresponding U.S. Pat. No. 4,808,587 to Go et al, and b) Japanese Patent Publication Nos. Hei-8/3046, Hei-8/3164 or Hei-8/3165, and their corresponding U.S. Pat. No. 5,776,942 to Furukawa et al. The disclosures of each of said Japanese Patent publications and said U.S. Pat. Nos. 4,808,587 and 5,776,942 are herein incorporated by reference in their entireties. For example, as disclosed in U.S. Pat. No. 4,808,587, pyrido[2,3-d]pyrimidine derivatives may be prepared using uracil derivatives as a starting material, or by subjecting pyrido[2,3-d]pyrimidine derivatives obtained thereby to further reactions such as catalytic reduction, halogenation, and the like. See U.S. Pat. No. 4,808,587, col. 1 line 38 to col. 2 line 4, and col. 2 line 68 to col. 4 line 30, herein incorporated by reference.

Methods for the production of the compounds of the present invention are further illustrated in detail by way of the following non-limiting examples. The starting materials may be purchased from Aldrich Chemical Co., Inc.; Furuka Chemical Inc.; Lancaster Synthesis Inc.; Maybridge Chemical Co., Ltd.; or Tokyo Kasei K.K. or may be synthesized by known methods mentioned in the literature such as *J. Org. Chem.*, 16, 1879 (1951); *J. Am. Chem. Soc.*, 75, 114 (1953); etc. In the following examples all parts, percentages and ratios are by weight, all temperatures are in ° C., and all reactions are conducted at about atmospheric pressure unless indicated to the contrary:

EXAMPLE 1

In this example, 7-amino-1,2,3,4-tetrahydro-1,3-diphenylpyrido[2,3-d]pyrimidine-2,4-dione (Compound 1) is produced using 6-amino-5-formyl-1,3-diphenyluracil as a reactant:

(A) Manufacture of 6-amino-5-formyl-1,3-diphenyluracil

A solution of 6-amino-1,3-diphenyluracil (10.0 g, 35.8 mmol) in dimethylformamide (100 mL) was cooled in an ice bath and phosphorus oxychloride (3.7 mL, 39.4 mmol) was dropped thereinto using a dropping funnel. The reaction mixture was stirred at room temperature for two hours and the reaction was stopped by adding 50 mL of water thereto. The pH was adjusted to 10 by a 1N solution of potassium hydroxide and stirring was carried out at room temperature for one additional hour. Crude crystals separated out therefrom were filtered and, after washing with 100 mL of water, the crude crystals were filtered. The resulting crude crystals were further recrystallized from hexane and ethyl acetate to give 6-amino-5-formyl-1,3-diphenyluracil (2.2 g) in a 40% yield.

Mp: 141–142° C.; $^1$H-NMR (DMSO-$d_6$) d: 7.29–7.61 (m, 10H), 9.80 (s, 1H), 9.98 (s, 1H); IR (KBr): 3309, 1730, 1662, 1647, 1616, 1516, 1491, 1365,770, 692cm$^{-1}$; Anal. Calcd for $C_{17}H_{13}N_3O_3$: C, 66.44; H, 4.26; N, 13.67; Found: C, 66.59; H, 4.24; N, 13.77; MS (EI) m/z: 307 [M$^+$], 279, 160, 132, 77.

(B) Manufacture of 7-amino-1,2,3,4-tetrahydro-1,3-diphenylpyrido[2,3-d]pyrimidine-2,4-dione (Compound 1)

A solution of 6-amino-5-formyl-1,3-diphenyluracil (5.0 g, 16.3 mmol) and 2-(triphenylphosphoranylidene)acetonitrile (5.9 g, 19.6 mmol) in anhydrous acetonitrile (100 mL) was heated to reflux for 24 hours in an argon stream. The reaction mixture was allowed to cool and the solvent was evaporated therefrom in vacuo. The crude crystals separated out therefrom were recrystallized from benzene to give 7-amino-1,2,3,4-tetrahydro-1,3-diphenylpyrido[2,3-d]pyrimidine-2,4-dione (2.4 g) in a 45% yield.

Mp: 162–163° C.; $^1$H-NMR (DMSO-$d_6$) d: 6.33 (d, 1H, J=9 Hz), 6.89 (br, 2H), 7.31–7.93 (m, 10H), 7.93 (d, 1H, J=9 Hz); IR (KBr): 3358, 1709, 1660, 1624, 1427, 1398, 694 cm$^{-1}$; Anal. Calcd for $C_{19}H_{14}N_4O_2$: C, 69.08; H, 4.27; N, 16.96; Found: C, 68.99; H, 4.37; N, 16.97 ; MS (EI) m/z: 330 [M$^+$], 211.

EXAMPLE 2

Appropriate starting materials were used in place of 6-amino-1,3-diphenyluracil which was the starting material in the above Example 1 and subjected to a manufacturing method for production of 7-amino-1,2,3,4-tetrahydro-1-phenylpyrido[2,3-d]pyrimidine-2,4-dione derivatives in the same manner as described in Example 1 whereupon Compounds 2 to 58 represented by the following formula (II) were manufactured. Details of the compounds are mentioned in Tables 1 and 2:

TABLE 1

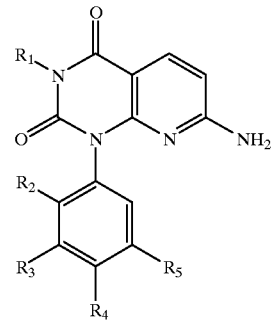

(II)

| Cpd. No. | $R_1$ | $R_2$ | $R_3$ | $R_4$ | $R_5$ | Mp (° C.) |
|---|---|---|---|---|---|---|
| 2 | Et | H | H | H | H | 218–219 |
| 3 | Pr | H | H | H | H | 198–199 |
| 4 | Bu | H | H | H | H | 209–211 |
| 5 | Et | H | OMe | H | OMe | 274–275 |
| 6 | Pr | H | OMe | H | OMe | 240–241 |
| 7 | Bu | H | OMe | H | OMe | 228–230 |
| 8 | Bn | H | OMe | H | OMe | 236–237 |
| 9 | Pr | H | H | OMe | H | 199–201 |
| 10 | Bu | H | H | OMe | H | 145–146 |
| 11 | Bn | H | H | OMe | H | 249–251 |
| 12 | 4-picolyl | H | H | OMe | H | 288–289 |
| 13 | Pr | H | OMe | OMe | H | 219–221 |
| 14 | Pr | OMe | H | H | OMe | 271–272 |
| 15 | iso-Bu | H | OMe | H | OMe | 206–208 |
| 16 | Bn | H | H | H | H | 261–262 |
| 17 | 4-picolyl | H | H | H | H | 280–281 |
| 18 | 4-picolyl | H | OMe | H | OMe | 225–227 |
| 19 | Bn | OMe | H | OMe | H | 254–256 |
| 20 | EtOEt | H | OMe | H | OMe | 225–227 |
| 21 | 3-butenyl | H | OMe | H | OMe | 215–217 |
| 22 | 4-picolyl | H | COOMe | H | H | 250–251 |
| 23 | 4-Cl—Bn | H | H | H | H | 240–241 |
| 24 | 3-(2-Me)picolyl | H | H | H | H | 286–288 |
| 25 | 2-picolyl | H | H | H | H | 236–237 |
| 26 | 3-picolyl | H | H | H | H | >300 |
| 27 | 3-Cl—Bn | H | H | H | H | 230–231 |
| 28 | 4-MeO—Bn | H | H | H | H | 248–250 |
| 29 | 4-F—Bn | H | H | H | H | 224–226 |
| 30 | 4-Me—Bn | H | H | H | H | 224–225 |

TABLE 2

| Cpd. No. | $R_1$ | $R_2$ | $R_3$ | $R_4$ | $R_5$ | Mp (° C.) |
|---|---|---|---|---|---|---|
| 31 | 3-NO$_2$—Bn | H | H | H | H | 247–248 |
| 32 | 2-Cl—Bn | H | H | H | H | 262–263 |
| 33 | 3-Me—Bn | H | H | H | H | 248–249 |
| 34 | 3,4-Cl$_2$—Bn | H | H | H | H | 245–246 |
| 35 | 3-MeO—Bn | H | H | H | H | 247–248 |
| 36 | 4-CF$_3$—Bn | H | H | H | H | 170–173 |
| 37 | 2-thienylmethyl | H | H | H | H | 279–282 |
| 38 | 2-furfuryl | H | H | H | H | 265–268 |
| 39 | 3-thienylmethyl | H | H | H | H | 276–280 |
| 40 | 3-(2-Cl-6-Me)picolyl | H | H | H | H | 243–245 |
| 41 | 4-COOMe—Bn | H | H | H | H | 242–244 |
| 42 | 2-dioxoranylmethyl | H | H | H | H | 265–267 |
| 43 | 4-COOH—Bn | H | H | H | H | >300 |
| 44 | Bn | H | Cl | H | H | 254–256 |
| 45 | 4-NO$_2$—Bn | H | H | H | H | 245–248 |
| 46 | 2-MeO—Bn | H | H | H | H | >300 |
| 47 | 3,5-(MeO)$_2$—Bn | H | H | H | H | 224–225 |
| 48 | 2-(5-Cl-thienyl)-methyl | H | H | H | H | 251–254 |
| 49 | Bn | H | F | H | F | 253–255 |
| 50 | (1-naphthyl)-methyl | H | H | H | H | >300 |
| 51 | 3,4-Me$_2$—Bn | H | H | H | H | 243–244 |
| 52 | Bn | H | OMe | H | H | 222–225 |
| 53 | 4-Br—Bn | H | H | H | H | 249–250 |
| 54 | 3-(2-Cl)picolyl | H | H | H | H | 258–259 |
| 55 | Bn | H | OBn | H | H | 213–215 |
| 56 | 5-(3-Me-isoxazolyl)-methyl | H | H | H | H | 250–251 |
| 57 | 4-(3,5-Me$_2$-isoxazolyl)-methyl | H | H | H | H | 253–254 |
| 58 | 5-Ph-pentyl | H | H | H | H | 135–137 |

EXAMPLE 3

Relaxing Action to Smooth Muscle of Airway of Guinea Pigs

A guinea pig was killed by draining out the blood, the airway was isolated, and four airway pieces having a width of about 1 cm cut along the cartilage were connected by silk yarn to prepare an airway smooth muscle sample. The sample was hung with a load of about 0.5 g in a 5-mL Magnus vessel filled with a Tyrode solution and aerated with a mixed gas (95% $O_2$ and 5% $CO_2$). After the sample was allowed to stand for 30 minutes to one hour, it was treated with histamine (final concentration: $10^{-5}$M) and the constriction was recorded on a recorder via an isotonic transducer. This was repeatedly treated with $10^{-5}$M of histamine and, after confirming that the constriction became constant, it was treated with $10^{-4}$M of histamine. After the maximum constriction reaction of the smooth muscle became constant, the test compound was added thereto starting from a low concentration cumulatively to investigate the relaxing action. A dose vs. reaction curve was prepared from the isotonic reaction of various concentrations of the test compound and $EC_{50}$, a concentration showing 50% of the maximum reaction, was determined. 7-Amino-1,3-diethyl-1,2,3,4-tetrahydropyrido-[2,3-d]pyrimidine-2,4-dione (Control Compound A; a compound mentioned in Japanese Laid-Open Patent Publication Hei-8/3046 and corresponding U.S. Pat. No. 5,776,942 to Furukawa et al), 5-amino-1,3,-diethyl-1,2,3,4-tetrahydropyrido[2,3-d]pyrimidine-1,4-dione (Control Compound B; a compound mentioned in Japanese Laid-Open Patent Publication Sho-63/45279, corresponding U.S. Pat. No. 4,808,587 to Go et al and in U.S. Pat. No. 5,776,942 to Furukawa et al) and theophylline were used as control agents. An example of the results is shown in Table 3. The compounds of the present invention showed better efficacy than the known bronchial dilators when tested by a relaxing action to airway smooth muscle isolated from guinea pigs.

TABLE 3

| Compound No. | $EC_{50}$ ($\mu$M) |
|---|---|
| 5 | 1.7 |
| 6 | 0.40 |
| 7 | 0.59 |
| 8 | 0.32 |
| 15 | 0.21 |
| 16 | 0.023 |
| 17 | 0.019 |
| 18 | 0.061 |
| 28 | 0.045 |
| 29 | 0.076 |
| 37 | 0.021 |
| 38 | 0.040 |
| 39 | 0.027 |
| Control Compound A | 1.01 |
| Control Compound B | 0.83 |
| theophylline | 51 |

EXAMPLE 4

Influence on Continuous Constriction of Airway Smooth Muscle of Rats

The back of the head of a rat was struck to cause a cerebral concussion, carotid arteries on both sides were immediately cut and the pulmonary main artery was isolated. The isolated artery was fully aerated with a mixed gas (95% $O_2$ and 5% $CO_2$), placed in a Krebs-Henselite solution warmed at 37° C., excessive tissues were removed as much as possible and a spiral sample (having a width of about 2 mm and a length of 15 mm) was prepared according to a method of Furchgott, et al. The blood vessel sample was hung with a load of about 0.5 g in a 5-mL Magnus vessel filled with a Krebs-Henseleit solution and aerated with a mixed gas (95% $O_2$ and 5% $CO_2$). After the sample was allowed to stand for 30 minutes

13 to one hour, it was treated with noradrenaline (final concentration: $10^{-7}$ M) and the constricting reaction was amplified via an amplifier for blood pressure using an FD pickup and recorded on a recorder. Noradrenaline ($10^{-7}$ M) was repeatedly applied and, after confirming that the constriction became constant, $10^{-7}$ M of noradrenaline was applied. After the maximum shrinking reaction of the smooth muscle became constant, the test compound was added thereto starting from a low concentration cumulatively to investigate the relaxing action. A dose vs. reaction curve was prepared from the isotonic reaction of various concentrations of the test compound and an $EC_{50}$, a concentration showing 50% of the maximum reaction, was determined. An example of the results is shown in Table 4. The compounds of the present invention showed little affect on blood vessels and high safety when tested for influence on a continuous constriction of smooth muscle of blood vessel isolated from rats.

TABLE 4

| Compound No. | $EC_{50}$ ($\mu$M) |
| --- | --- |
| 5 | >100 |
| 6 | >100 |
| 15 | >100 |
| 16 | 50.1 |
| 18 | >100 |

14 by means of the forefeet and, if their reaction at that time for climbing up the wire took a longer time than the non-administered group, that was evaluated as (+).

3) Passiveness: When mice were hung by holding the neck of the mice between two fingers and, if the mice did not move so much at that time, that was marked as (+).

4) Blepharoptosis: If ¼ or more was closed as compared with the non-administered group, that was evaluated as (+).

5) Salivation: If salivation was noted a little around the mouth, that was evaluated as (+).

6) Death: If dead case was noted, that was mentioned as such.

5-Amino-1,3-diethyl-1,2,3,4-tetrahydropyrido[2,3-d]-pyrimidine-2,4-dione (Control Compound B; a compound mentioned in Japanese Laid-Open Patent Publication Sho-63/45279 and in U.S. Pat. Nos. 4,808,587 and 5,776,942) was used as a control drug. An example of the results is shown in Table 5. When the compounds of the present invention were tested in terms of an influence on the general symptoms of mice, they showed very high safety as compared with the known bronchial dilator.

TABLE 5

| Compound No. | Administered dose (mg/kg) | Suppression of spontaneous motility | Muscle relaxation | Passiveness | Blepharoptosis | Salivation | Death |
| --- | --- | --- | --- | --- | --- | --- | --- |
| 5 | 1000 | (+) × 2 | (+) × 3 | (−) | (+) × 3 | (−) | 0 |
| 6 | 300 | (+) × 1 | (−) | (−) | (+) × 1 | (−) | 0 |
|   | 1000 | (+) × 2 | (+) × 2 | (−) | (+) × 2 | (−) | 0 |
| 7 | 300 | (+) × 2 | (+) × 2 | (−) | (+) × 1 | (−) | 0 |
|   |   | (+) × 1 |   |   |   |   |   |
|   | 1000 | (+) × 3 | (−) | (−) | (−) |   | 0 |
|   |   | (++) × 1 |   |   |   |   |   |
| Control Compd B | 100 | (+) × 3 | (+) × 3 | (+) × 1 | (+) × 2 | (−) | 0 |
|   |   |   | (+) × 4 | (+) × 1 | (+) × 2 |   |   |
|   | 300 | (+) × 3 |   |   |   | (−) | 0 |
|   |   |   | (++) × 1 | (++) × 2 | (++) × 1 |   |   |

EXAMPLE 5

Influence on General Symptoms of Mice

Mice having no abnormality in their appearance before administration of the test drugs were selected, and five mice were used for each group. Oral administration of the test compound was carried out and, 30 minutes, one hour and two hours thereafter, observations were conducted according to the modified method of Irwin's method for observing the general symptoms of mice. Degree of the symptom was evaluated in terms of (+) and (−) and, when the symptom was apparently severe, it was mentioned as (++). Also, death was observed until the next day of the administration.

1) Suppression of spontaneous motility: When mice were transferred from a home cage to a cage for symptom observation and, if motion of the mice was less than the non-administered group at that time, that was evaluated as (+).

2) Muscle relaxation: When forefeet of mice were hung on a wire stretched horizontally so that the mice were hung

EXAMPLE 6

Concentration in Blood of Guinea Pigs

Each test substance was orally administered at a dose of 30 mg/kg. It was suspended in 1% methyl cellulose and made into a preparation so as to make the administering dose 5 mL/kg. A group consisted of four animals and blood was collected after 30 minutes, 1 hour, 2 hours, 4 hours, 6 hours and 24 hours from the administration. (A feed was given after collection of the blood after 6 hours). Thus, each about 200 mL (corresponding to four capillary tubes) of blood were collected with intervals using a heparintreated capillary tube and plasma was separated by a hematocrit centrifuge to prepare a plasma sample. A plasma sample of about 100 mL was preserved at −80° C. until the measurement. Methanol (200 mL) was added to 100 mL of the plasma followed by mixing, the mixture was centrifuged at 1500×g for ten minutes at 40° C. and the separated supernatant liquid was filtered through a membrane filter of 0.5 mm. The filtrate was used as a sample for an HPLC, analyzed under the analyzing condition that the column was 100 mm×4.6 mm (inner diameter) of TSK-gel Super ODS, the flow rate was 1.0 mL/minute, the column temperature was 40° C., an injection amount was 6 mL, detection was done by UV of 225 nm and the mobile phase was water-acetonitrile (75:25 in terms of % by volume) and the maximum concentration in blood ($C_{max}$), time required for achieving the maximum concentration in blood ($T_{max}$), half life in blood ($T_{1/2}$) and area under a curve of concentration in blood vs. time (AUC 0-lim) were determined. RS-25344 (*Cell Signalling*, 7(5), 527 (1995); *Mol. Pharmacol.*, 48, 616 (1995)) and CR-77059 (*J. Med. Chem.*, 34, 624 (1991); *J. Pharmacol. Exp. Ther.*, 272, 3,1313 (1995)) were used as control drugs. An example of the results is shown in Table 6. When the behavior in blood of guinea pigs was tested, the compounds of the present invention showed a good transfer into blood and a long half life exhibiting a favorable behavior in vivo as compared with known xanthine-related compounds.

TABLE 6

| Compound No. | $C_{max}$ (μg/mL) | $T_{max}$ (h) | $T_{1/2}$ (h) | AUC 0-lim (μg h/mL) |
|---|---|---|---|---|
| 5 | 30.0 | 3.0 | 12.1 | 458.2 |
| 6 | 13.7 | 4.0 | 28.4 | 255.8 |
| 7 | 1.6 | 15.0 | 131.4 | 28.6 |
| 15 | 10.1 | 2.3 | 9.8 | 133.8 |
| RS-25344 | (less than identification limit) | | | |
| CP-77059 | (less than identification limit) | | | |

As shown in Table 3, the 7-amino-1-phenylpyrido[2,3-d]pyrimidine-2,4-dione derivatives of the present invention exhibit better bronchial dilating action than the known bronchial dilators. Accordingly, the compounds of the present invention are useful as therapeutic agents for bronchial asthma.

It is also apparent from Tables 4 and 5 that the compounds of the present invention show far higher safety than the known bronchial dilators. It is further apparent from Table 6 that the compounds of the present invention show good transfer into blood and a long half life in blood which are not available in the known xanthine-related compounds whereby a favorable behavior in vivo is achieved. Accordingly, the compounds of the present invention exhibit unexpectedly superior characteristics as pharmaceuticals than the known compounds.

As mentioned above, the compounds of the present invention exhibit an excellent bronchial dilating action, with a high degree of safety and little side effects. Moreover, the compounds of the present invention exhibit a favorable behavior in vivo and their usefulness as pharmaceuticals is quite high.

We claim:

1. A 7-amino-1-phenylpyrido[2,3-d]pyrimidine-2,4-dione compound represented by the formula (I) or a pharmaceutically acceptable salt or hydrate thereof:

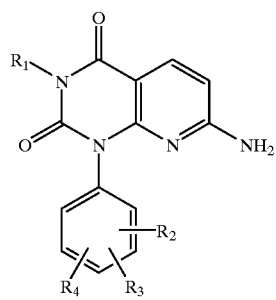

wherein $R_1$ is hydrogen, lower alkenyl, phenyl or lower alkyl which is optionally substituted with a substituent selected from the following substituents (a) to (I);
(a) oxo,
(b) lower alkoxy,
(c) phenyl which is optionally substituted with at least one member selected from the group consisting of lower alkyl, lower alkoxy, carboxyl, lower alkoxycarbonyl, mercapto, halogen, trifluoromethyl, and nitro,
(d) naphthyl,
(e) furyl,
(f) isoxazolyl which is optionally substituted with one or more lower alkyl,
(g) pyridyl which is optionally substituted with at least one member selected from the group consisting of lower alkyl and halogen,
(h) thienyl which is optionally substituted with halogen, and
(i) 1,3-dioxolanyl;
and $R_2$, $R_3$ and $R_4$ each independently is hydrogen, halogen, lower alkoxy, benzyloxy, carboxyl or lower alkoxycarbonyl.

2. A 7-amino-1-phenylpyrido[2,3-d]pyrimidine-2,4-dione compound as claimed in claim 1 wherein $R_2$ is hydrogen.

3. A 7-amino-1-phenylpyrido[2,3-d]pyrimidine-2,4-dione compound as claimed in claim 2 wherein $R_3$ is lower alkoxy.

4. A 7-amino-1-phenylpyrido[2,3-d]pyrimidine-2,4-dione compound as claimed in claim 3 wherein $R_3$ is substituted at a meta position.

5. A 7-amino-1-phenylpyrido[2,3-d]pyrimidine-2,4-dione compound as claimed in claim 3 wherein the lower alkoxy is methoxy.

6. A 7-amino-1-phenylpyrido[2,3-d]pyrimidine-2,4-dione compound as claimed in claim 4 wherein the lower alkoxy is methoxy.

7. A 7-amino-1-phenylpyrido[2,3-d]pyrimidine-2,4-dione compound as claimed in claim 3 wherein $R_4$ is lower alkoxy.

8. A 7-amino-1-phenylpyrido[2,3-d]pyrimidine-2,4-dione compound as claimed in claim 7 wherein $R_4$ is substituted at a meta position.

9. A 7-amino-1-phenylpyrido[2,3-d]pyrimidine-2,4-dione compound as claimed in claim 7 wherein the lower alkoxy is methoxy.

10. A 7-amino-1-phenylpyrido[2,3-d]pyrimidine-2,4-dione compound as claimed in claim 8 wherein the lower alkoxy is methoxy.

11. A 7-amino-1-phenylpyrido[2,3-d]pyrimidine-2,4-dione compound as claimed in claim 1 wherein $R_1$ is lower alkyl.

12. A 7-amino-1-phenylpyrido[2,3-d]pyrimidine-2,4-dione compound as claimed in claim 2 wherein $R_1$ is lower alkyl.

13. A 7-amino-1-phenylpyrido[2,3-d]pyrimidine-2,4-dione compound as claimed in claim 3 wherein $R_1$ is lower alkyl.

14. A 7-amino-1-phenylpyrido[2,3-d]pyrimidine-2,4-dione compound as claimed in claim 4 wherein $R_1$ is lower alkyl.

15. A 7-amino-1-phenylpyrido[2,3-d]pyrimidine-2,4-dione compound as claimed in claim 1 wherein $R_1$ is lower alkyl and at least one of $R_2$, $R_3$ and $R_4$ is alkoxy.

16. A 7-amino-1-phenylpyrido[2,3-d]pyrimidine-2,4-dione compound as claimed in claim 1 wherein $R_1$ is isobutyl.

17. A 7-amino-1-phenylpyrido[2,3-d]pyrimidine-2,4-dione compound as claimed in claim 1 wherein $R_1$ is propyl.

18. A 7-amino-1-phenylpyrido[2,3-d]pyrimidine-2,4-dione compound as claimed in claim 1 wherein $R_1$ is a lower alkyl which is optionally substituted with a substituent selected from said substituents (a) to (i).

19. A 7-amino-1-phenylpyrido[2,3-d]pyrimidine-2,4-dione compound as claimed in claim 1 wherein $R_1$ is benzyl which is optionally substituted with at least one member selected from the group consisting of lower alkyl, lower alkoxy, carboxyl, lower alkoxycarbonyl, mercapto, halogen, trifluoromethyl, and nitro.

20. 7-amino-1-(3,5-dimethoxyphenyl)-1,2,3,4-tetrahydro-3-propylpyrido [2,3-d]pyrimidine-2,4-dione, or a pharmaceutically acceptable salt or hydrate thereof.

21. A pharmaceutical composition for the treatment of bronchial asthma comprising a pharmaceutically effective amount of or more than one 7-amino-1-phenylpyrido[2,3-d]pyrimidine-2,4-dione compound as claimed in claim 1.

22. A pharmaceutical composition as claimed in claim 21 wherein $R_2$ is hydrogen and $R_3$ is lower alkoxy.

23. A pharmaceutical composition as claimed in claim 21 wherein $R_2$ is hydrogen and each of $R_3$ and $R_4$ is lower alkoxy.

24. A pharmaceutical composition as claimed in claim 23 wherein $R_1$ is lower alkyl and each of $R_3$ and $R_4$ is methoxy.

25. A method for the treatment of bronchial asthma comprising administering to a patient in need of such treatment a pharmaceutically effective amount of at least one 7-amino-1-phenylpyrido[2,3-d]pyrimidine2,4-dione compound as claimed in claim 1.

26. A 7-amino-1-phenylpyrido[2,3-d]pyrimidine-2,4-dione derivative as claimed in claim 1 wherein at least one of $R_2$, $R_3$ and $R_4$ is halogen, lower alkoxy, benzyloxy, carboxyl or lower alkoxycarbonyl.

27. A 7-amino-1-phenylpyrido[2,3-d]pyrimidine-2,4-dione derivative as claimed in claim 1 wherein $R_1$ is lower alkenyl, phenyl or substituted lower alkyl.

* * * * *